(12) United States Patent
De Gunzburg et al.

(10) Patent No.: US 10,988,749 B2
(45) Date of Patent: Apr. 27, 2021

(54) BETA-LACTAMASE VARIANTS

(71) Applicants: DA VOLTERRA, Paris (FR);
BIOASTER, Lyons (FR)

(72) Inventors: Jean De Gunzburg, London (GB);
Jean-Denis Docquier, Sovicille (IT)

(73) Assignees: DA VOLTERRA, Paris (FR);
BIOASTER, Lyons (FR)

( * ) Notice: Subject to any disclaimer, the term of this patent is extended or adjusted under 35 U.S.C. 154(b) by 83 days.

(21) Appl. No.: 16/078,037

(22) PCT Filed: Feb. 22, 2017

(86) PCT No.: PCT/EP2017/053985
§ 371 (c)(1),
(2) Date: Aug. 21, 2018

(87) PCT Pub. No.: WO2017/144495
PCT Pub. Date: Aug. 31, 2017

(65) Prior Publication Data
US 2019/0048331 A1     Feb. 14, 2019

(30) Foreign Application Priority Data
Feb. 23, 2016   (EP) ..................................... 16305208

(51) Int. Cl.
| | | |
|---|---|---|
| *C12N 9/86* | (2006.01) | |
| *A61K 9/00* | (2006.01) | |
| *A61K 31/407* | (2006.01) | |
| *A61K 31/496* | (2006.01) | |
| *A61K 31/546* | (2006.01) | |
| *A61K 38/50* | (2006.01) | |

(52) U.S. Cl.
CPC .............. *C12N 9/86* (2013.01); *A61K 9/0053* (2013.01); *A61K 31/407* (2013.01); *A61K 31/496* (2013.01); *A61K 31/546* (2013.01); *A61K 38/50* (2013.01); *C12Y 305/02006* (2013.01)

(58) Field of Classification Search
CPC .............. C12N 9/86; C12Y 305/02006; A61K 9/0053; A61K 31/407; A61K 31/496; A61K 31/546; A61K 38/50
See application file for complete search history.

(56) References Cited

U.S. PATENT DOCUMENTS

| | | |
|---|---|---|
| 2008/0199528 A1 | 8/2008 | Andremont et al. |
| 2015/0031063 A1* | 1/2015 | Charretier .......... G01N 33/6848 435/23 |

FOREIGN PATENT DOCUMENTS

| | | | |
|---|---|---|---|
| CN | 102 757 950 A1 | 10/2012 | |
| CN | 102757950 A | * 10/2012 | |
| WO | 2007/147945 A1 | 12/2007 | |
| WO | WO-2012143535 A2 | * 10/2012 | |
| WO | 2015/161243 A2 | 10/2015 | |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36): 11643-50.*
UniProt Accession No. _U3N1N3, metallo-beta-lactamase VIM-2, created Dec. 11, 2013.*
Schmidtke et al. Model System To Evaluate the Effect of ampD Mutations on AmpC-Mediated β-Lactam Resistance. Antimicrobial Agents and Chemotherapy (2006), 50(6): 2030-2037.*
Database Uniprot, Oct. 2013 (Oct. 16, 2013), Metallobetalactamase VIM-2 Fragment, Uniprot:S5LUZ5.
Database Uniprot, Oct. 16, 2013 (Oct. 16, 2013), Metal-lobetalactamase VIM-2 Fragment, Uniprot:S5MBM8.
Database Geneseq, Jun. 29, 2013 (Jun. 20, 2013), "Metallo-beta-lactamase-1 VIM-2.", EBI accession No. GSP: BAN76004.
Database Geneseq, Dec. 20, 2012 (Dec. 20, 2012), Microorganism detection-related resistant marker protein, SEQ:312., EBI accession No. GSP:BAE47483.
Borgianni et al, Mutational Analysis of VIM-2 Reveals an Essential Determinant for Metallo-Lactamase Stability and Folding, Antimicrobial Agents and Chemotherapy, vol. 54, No. 8 May 24, 2010 (May 24, 2010), pp. 3197-3204.
K. Bush et al: "Updated Functional Classification of -Lactamases", Antimicrobial Agents and Chemotherapy, vol. 54, No. 3, Dec. 7, 2009 (Dec. 7, 2009), pp. 969-976.
Garau G et al: "Update of the Standard Numbering Scheme for Class B beta-Lactamases", Antimicrobial Agents and Chemotherapy, American Society for Microbiology, US, vol. 48, No. 7, Jul. 1, 2004 (Jul. 1, 2004), pp. 2347-2349.

* cited by examiner

*Primary Examiner* — Iqbal H Chowdhury
(74) *Attorney, Agent, or Firm* — Arrigo, Lee, Guttman & Mouta-Bellum LLP

(57) ABSTRACT

The present invention relates to an isolated polypeptide having beta-lactamase activity and nucleic acid sequences encoding the polypeptide. The isolated polypeptide of the invention is a VIM-2 variant with improved properties such as improved protease stability.

16 Claims, 1 Drawing Sheet
Specification includes a Sequence Listing.

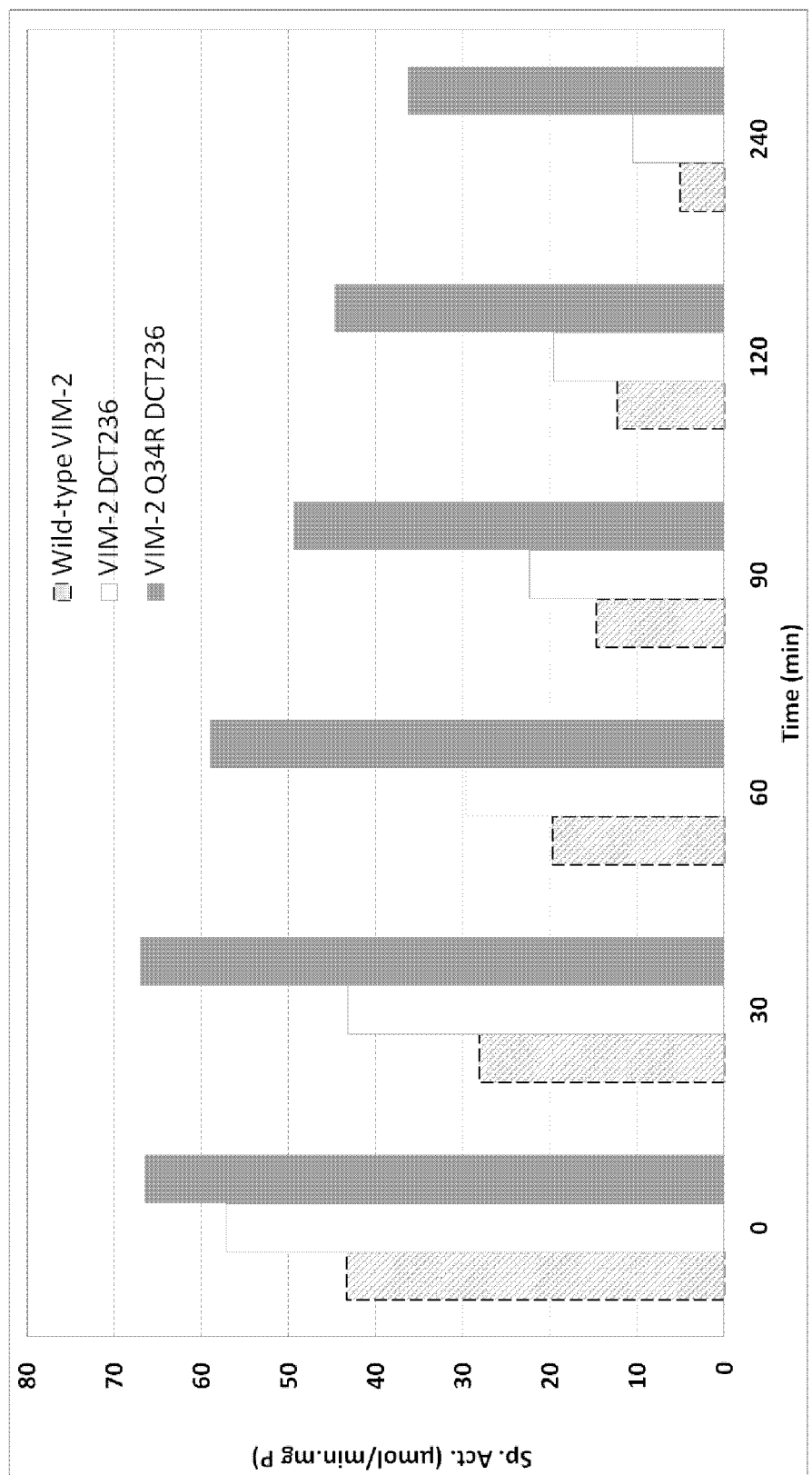

BETA-LACTAMASE VARIANTS

CROSS-REFERENCE TO RELATED APPLICATIONS

This application is the U.S. Natl. Stage of International Application PCT/EP2017/053985, filed Feb. 22, 2017, which claims the benefit of European Application EP 16305208.7, filed Feb. 23, 2016.

SEQUENCE LISTING

The instant application contains a Sequence Listing which has been submitted electronically in ASCII format and is hereby incorporated by reference in its entirety. Said ASCII copy, created on Jul. 9, 2018, is named B2184PC00-SEQ LIST_ST25.txt and is 11,037 bytes in size.

FIELD OF THE INVENTION

The present invention relates to an isolated polypeptide having beta-lactamase activity and nucleic acid sequences encoding the polypeptide. The isolated polypeptide of the invention is a subclass B1 metallo-beta-lactamase belonging to the VIM-type subgroup variant with improved properties such as improved protease stability.

BACKGROUND OF THE INVENTION

Many antibacterial products, in particular antibiotics, may be used in the treatment of bacterial infections. However, antibiotics do not only attack pathogens at the infection site, but also affect the normal bacterial flora which can be found in healthy subjects, and in particular in the gut. The alteration by antibiotics of the colonic commensal flora (also called intestinal microbiota), which is composed of more than ten trillion bacteria from over 500 species, may lead to adverse side effects such as selection of resistant bacteria and potential colonization by resistant bacteria, disruption of normal digestive processes, colonization and infection of the intestine by opportunistic intestinal pathogens such as *Clostridium difficile*, antibiotic-associated diarrhea or other diseases related to the intestinal dysbiosis. These side effects can be reduced by administering enzymes capable of degrading residual antibiotics in the intestine, more particularly in the late ileum and colon. This approach is described in particular in WO2004/016248 or US20050249716.

However, enzymes are fragile macromolecules sensitive to a number of physico-chemical factors, such as the presence of proteases leading to their degradation, temperature, ion strength, availability of metal cofactors or presence of chelators. In addition, enzymes with improved specific activity would be advantageous in order to increase their efficiency and/or reduce the amount necessary to use for obtaining an efficient degradation of residual antibiotics in a patient in need thereof. Finally, it would be advantageous to obtain improved production yields for such antibiotic-degrading enzymes.

SUMMARY OF THE INVENTION

The present invention provides novel variants of the VIM-2 metallo-beta-lactamase. Specifically, the present invention relates to a polypeptide having beta-lactamase activity, which comprises an amino acid sequence having at least 70% sequence identity to the amino acid sequence shown in SEQ ID NO:1 (which is the sequence of wild-type VIM-2 without its natural N-terminal signal peptide), said polypeptide having a truncation at its C-terminal end as compared to SEQ ID NO:1. The polypeptide of the invention has an improved protease resistance, in particular digestive protease resistance, such as trypsin resistance, compared to the wild-type VIM-2 enzyme. The variant may also comprise at least one substitution in position 34, wherein the position corresponds to amino acid number 34 in the sequence of the VIM-2 beta-lactamase of SEQ ID NO:1.

Extensive research conducted by the inventors led to identify C-terminal end deletion variants of the VIM-2 enzyme with increased stability against proteases while preserving the beta-lactam-hydrolyzing activity of the enzyme. This was surprising as deletions or alterations in the structure of the enzyme very often lead to a full or partial loss of enzymatic activity.

Even more surprisingly, it was discovered that amino acid substitutions at position 34 in SEQ ID NO:1 exhibited increased enzymatic activity against a number of beta-lactam antibiotics. This increased activity compared with the wild-type enzyme is preserved when combined with a C-terminal deletion according to the invention, thus combining both increased activity and increased protease resistance reported herein.

The invention thus more specifically relates to a polypeptide variant of VIM-2 wherein the C-terminal end is truncated from position 236 and comprises a substitution at position 34. In a particular embodiment, said substitution is Q34R.

The VIM-2 variant according to the invention presents an improved property with respect to resistance to proteases, in particular to digestive proteases, as compared with wild-type VIM-2 of SEQ ID NO:1, which may be determined by monitoring the enzyme activity (by means of in vitro enzyme assays as described below) and/or integrity (e.g. by means of mass spectrometry analysis) after incubation with either purified proteases such as trypsin, chymotrypsin or the like or with intestinal medium from piglets, pigs, other mammals or other animals.

Bacteria producing the VIM-2 variant according to the invention may present an improved property with respect to a Minimal Inhibitory Concentration (MIC) for at least one beta-lactam antibiotic such as, but not exclusively, ampicillin, piperacillin, ticarcillin, temocillin, cephalothin, cefoxitin, cefuroxime, cefotaxime, ceftazidime, cefepime, ceftriaxone, ceftaroline, cefotetan, imipenem, meropenem and ertapenem, as compared to a MIC of the same bacteria producing wild-type VIM-2 of SEQ ID NO:1, which may be determined by using standard in vitro susceptibility testing methods, such as the microdilution broth method (Clinical Laboratory Standard Institute, document M07-A10: Methods for Dilution Antimicrobial Susceptibility Tests for Bacteria That Grow Aerobically; Approved Standard—Tenth Edition). In the context of the present invention, the expression "improved property with respect to a Minimal Inhibitory Concentration (MIC)" denotes a MIC which is increased for the bacteria producing the VIM-2 variant, for example a MIC increased 2-fold or more, compared with the same bacteria producing the wild-type VIM-2.

The VIM-2 variant according to the invention may also present an improved property with respect to stability (in particular thermal stability), as compared with wild-type VIM-2 of SEQ ID NO:1, which may be determined by monitoring the enzyme residual activity after incubation of the protein sample at temperatures ranging from 45 to 75° C. for up to two hours, and in particular at 65° C. for 45 min.

The VIM-2 variant according to the invention may also present an improved property with respect to stability to proteases, as compared with wild-type VIM-2 of SEQ ID NO:1, which may be determined by monitoring the enzyme residual activity after incubation of the protein sample for different durations in a buffer containing purified proteases, for example trypsin. Representative means for monitoring the enzyme residual activity include, for example, those described below and in the example section.

The VIM-2 variant according to the invention may also present an improved property with respect to stability in intestinal medium, particularly jejunal, ileal and caecal medium as compared with wild-type VIM-2 of SEQ ID NO:1, which may be determined by monitoring the enzyme residual activity after incubation of the protein sample for different durations in intestinal medium, for example ileal medium. Representative means for monitoring the enzyme residual activity include, for example, those described below and in the example section.

The VIM-2 variant according to the invention may also present an improved property with respect to its hydrolyzing specific activity on one or more beta-lactam substrate(s) (such as specific beta-lactam antibiotic(s)), as compared to the activity shown by the wild-type VIM-2 of SEQ ID NO:1, which may be determined by in vitro enzyme assays, in which the time-dependent variation of a beta-lactam substrate concentration is monitored spectrophotometrically in the presence of protein samples containing the wild-type VIM-2 or the VIM-2 variant.

The VIM-2 variant according to the invention may also present an improved property with respect to an increased production level thereof in recombinant bacteria or other suitable hosts, as compared to the production level of wild-type VIM-2 of SEQ ID NO:1, which may be determined by in vitro enzyme assays, for example assays carried out as described above with extracts obtained from bacterial cultures producing the wild-type VIM-2 or the variants thereof. In a particular embodiment, the extract is obtained by bacterial lysis or is a cell (prokaryotic or eukaryotic) culture extract (in case of a secreted enzyme).

In a particular embodiment, the polypeptide of the invention comprises or consists of the sequence selected from the group consisting of SEQ ID NO:3 to SEQ ID NO:6

```
SEQ ID NO: 3
MDSSGEYPTVSEIPVGEVRLYQIADGVWSHIATQSFDGAVYPSNGLIVRD

GDELLLIDTAWGAKNTAALLAEIEKQIGLPVTRAVSTHFHDDRVGGVDVL

RAAGVATYASPSTRRLAEVEGNEIPTHSLEGLSSSGDAVRFGPVELFYPG

AAHSTDNLVVYVPSASVLYGGCAIYELSRTSAGNVADADLAEWPTSIERI

QQHYPEAQFVIPGHGLPGGLDLLKHTTNVVKAHTN

SEQ ID NO: 4:
MDSSGEYPTVSEIPVGEVRLYQIADGVWSHIATRSFDGAVYPSNGLIVRD

GDELLLIDTAWGAKNTAALLAEIEKQIGLPVTRAVSTHFHDDRVGGVDVL

RAAGVATYASPSTRRLAEVEGNEIPTHSLEGLSSSGDAVRFGPVELFYPG

AAHSTDNLVVYVPSASVLYGGCAIYELSRTSAGNVADADLAEWPTSIERI

QQHYPEAQFVIPGHGLPGGLDLLKHTTNVVKAHTN

SEQ ID NO: 5:
VDSSGEYPTVSEIPVGEVRLYQIADGVWSHIATQSFDGAVYPSNGLIVRD

GDELLLIDTAWGAKNTAALLAEIEKQIGLPVTRAVSTHFHDDRVGGVDVL
```

```
-continued
RAAGVATYASPSTRRLAEVEGNEIPTHSLEGLSSSGDAVRFGPVELFYPG

AAHSTDNLVVYVPSASVLYGGCAIYELSRTSAGNVADADLAEWPTSIERI

QQHYPEAQFVIPGHGLPGGLDLLKHTTNVVKAHTN

SEQ ID NO: 6:
VDSSGEYPTVSEIPVGEVRLYQIADGVWSHIATRSFDGAVYPSNGLIVRD

GDELLLIDTAWGAKNTAALLAEIEKQIGLPVTRAVSTHFHDDRVGGVDVL

RAAGVATYASPSTRRLAEVEGNEIPTHSLEGLSSSGDAVRFGPVELFYPG

AAHSTDNLVVYVPSASVLYGGCAIYELSRTSAGNVADADLAEWPTSIERI

QQHYPEAQFVIPGHGLPGGLDLLKHTTNVVKAHTN
```

The present invention also relates to a nucleic acid sequence encoding the VIM-2 polypeptide variant of the invention, nucleic acid constructs comprising the same, recombinant viruses or host cells (prokaryotic and eukaryotic) comprising the nucleic acid sequence or the nucleic acid construct according to the invention, and methods for their production.

The invention further relates to a composition comprising the polypeptide variant according to the invention. In a particular embodiment, the composition is orally administrable and is able to release the polypeptide in a desired part of the intestine of a subject in need thereof. Preferably, the desired part is the jejunum, ileum, caecum or colon.

In a further embodiment, the invention relates to a recombinant host cell, prokaryotic or eukaryotic, or organism producing the polypeptide that may be administered to a subject and release the polypeptide in the desired part of the intestine of said subject in need thereof. Preferably the polypeptide is released in the ileum, caecum or colon, preferably the caecum or colon.

A further aspect of the invention is a kit-of-parts for separate, sequential or simultaneous administration of the polypeptide according to the invention and a beta-lactam compound, for example beta-lactam antibiotic, which is sensitive to said polypeptide of the kit-of-parts. In a particular embodiment, both the polypeptide and the antibiotic are orally administrable. In another embodiment, the polypeptide and the antibiotic are administered by different routes, for instance the polypeptide is orally administrable and the antibiotic is parenterally administrable, such as by injection like an intravenous, intra-arterial, intramuscular, subcutaneous or intraperitoneal injection. In a particular embodiment, the polypeptide is administered before or after, in particular before, the antibiotic The present invention also relates to methods of therapy implementing the polypeptide of the invention. Thus the invention provides the polypeptide of the invention, which is a VIM-2 variant, for use as a medicament. It more specifically provides the use of said polypeptide or a composition or a kit-of-parts containing the same, in a method for inactivating a beta-lactam antibiotic in a subject in need thereof. The invention also relates to the use of the polypeptide, the composition or the kit-of-parts of the invention, in a method for the treatment of a bacterial infection which is caused by bacteria which are susceptible to a beta-lactam antibiotic. More particularly, the bacterial infection is treated by using a combination of the polypeptide of the invention and of a beta-lactam antibiotic which is sensitive to said polypeptide, thereby having the infection treated thanks to the beta-lactam antibiotic whereas any unwanted residual antibiotic is eliminated from the intestine, and in a specific embodiment specifically from the jejunum, ileum, caecum and colon, thanks to the polypeptide of the invention. In this particular embodiment, the polypeptide is preferably formulated in a composition that is able to release the polypeptide in a desired part of the intestine of a subject in need of such bacterial infection treatment, wherein the desired part of the intestine is preferably the jejunum, the ileum, the caecum or the colon, most preferably the ileum, the caecum or the colon. The polypeptide may be produced by recombinant host cells (prokaryotic or eukaryotic) or organisms that are orally administered to the subject in need of such bacterial infection treatment, and release the polypeptide in the desired part of the intestine, in particular in the ileum, caecum or colon.

DETAILED DESCRIPTION OF THE INVENTION

The present invention provides novel variants of the VIM-2 metallo-beta-lactamase. Therefore, the sequence of the polypeptide of the invention is not identical to the sequence of VIM-2 which is shown in SEQ ID NO:1 in that it differs from VIM-2 by at least one amino-acid modification as compared to SEQ ID NO:1.

The sequence shown in SEQ ID NO:1 is the amino acid sequence of wild-type VIM-2 that has undergone N-terminal signal peptide cleavage (i.e. the sequence of wild-type VIM-2 without its signal peptide).

```
SEQ ID NO: 1:
VDSSGEYPTVSEIPVGEVRLYQIADGVWSHIATQSFDGAVYPSNGLIVRD

GDELLLIDTAWGAKNTAALLAEIEKQIGLPVTRAVSTHFHDDRVGGVDVL

RAAGVATYASPSTRRLAEVEGNEIPTHSLEGLSSSGDAVRFGPVELFYPG

AAHSTDNLVVYVPSASVLYGGCAIYELSRTSAGNVADADLAEWPTSIERI

QQHYPEAQFVIPGHGLPGGLDLLKHTTNVVKAHTNRSVVE
```

This sequence thus starts with a valine residue at its N-terminal end. However, in particular embodiments of the invention, this first valine residue may be replaced by a methionine residue. For example, in cases where the VIM-2 protein or its variant are produced without an N-terminal signal peptide from an expression cassette, an initiation codon encoding a methionine residue may be introduced in the VIM-2 or VIM-2 variant coding gene instead of a codon encoding a valine residue. Accordingly, in a particular embodiment of the invention, the polypeptide of the invention comprises the V1M substitution.

The polypeptide of the present invention shares at least 70% sequence identity with the amino acid sequence shown in SEQ ID NO:1, and wherein said polypeptide is truncated at its C-terminal end (otherwise termed as "C-terminal truncation") as compared to the sequence shown in SEQ ID NO:1. In a particular embodiment, said C-terminal truncation occurs by removal of residues at positions 237 to 240. In the context of the present invention, a truncation "from position X" means that the residue in the X position, and residues following said residue in the X position towards the C-terminal end are missing from the truncated polypeptide. In a further particular embodiment, the truncation is from position 236 (i.e. residues 236 to 240 of SEQ ID NO:1 are removed). In another particular embodiment, the truncation is from position 235 (i.e. residues 235 to 240 of SEQ ID NO:1 are removed).

In a further embodiment, the polypeptide comprises an amino acid sequence having at least 70% sequence identity to SEQ ID NO:1 and a C-terminal truncation of exactly five residues from position 236 to 240 of SEQ ID NO:1. By "exactly five residues" is meant no more than five residues and no less than five residues.

In addition to improved resistance to proteases, said polypeptide of the invention has, or may have one or more of the following properties as compared to the wild-type VIM-2 enzyme: (i) improved stability (in particular stability in the intestinal medium), (ii) improved spectrum of action on beta-lactam compounds in particular beta-lactam antibiotics, (i.e. the polypeptide of the invention is able to inactivate a greater number of different beta-lactam compounds (such as antibiotics) as compared to the wild-type VIM-2 enzyme, or it is able to inactivate beta-lactam compounds not susceptible to the wild-type VIM-2 enzyme), (iii) improved enzymatic activity (in particular decreased antibiotic inactivation time), and (iv) improved production yield.

In a further embodiment, the polypeptide of the invention comprises one or more mutations, in addition to the truncation of the C-terminal end as described above. For example, the variant polypeptide may further comprise a modification at position 34, wherein the position corresponds to amino acid position 34 in the sequence of the VIM-2 beta-lactamase of SEQ ID NO:1. In a particular embodiment, the variant polypeptide comprises at least the Q34R substitution.

In the context of the present invention, "Q34R" means that the amino acid at position 34 in SEQ ID NO:1, which is Q in wild-type VIM-2, is replaced by R.

In the present invention, amino acids are represented using either the well-known three letter code or one letter code as summarized in the table below.

| Amino acid | Three letter code | One letter code |
| --- | --- | --- |
| alanine | ala | A |
| arginine | arg | R |
| asparagine | asn | N |
| aspartic acid | asp | D |
| cysteine | cys | C |
| glutamic acid | glu | E |
| glutamine | gln | Q |
| glycine | gly | G |
| histidine | his | H |
| isoleucine | ile | I |
| leucine | leu | L |
| lysine | lys | K |
| methionine | met | M |
| phenylalanine | phe | F |
| proline | pro | P |
| serine | ser | S |
| threonine | thr | T |
| tryptophan | trp | W |
| tyrosine | tyr | Y |
| valine | val | V |

According to the present invention, a beta-lactamase is a polypeptide having beta-lactamase activity, i.e. an enzyme which catalyzes the irreversible hydrolysis of the amide bond of the beta-lactam ring of compounds such as beta-lactam antibiotics, to create an ineffective beta-lactam product, i.e. defective of antibiotic activity.

In the context of the present invention, the VIM-2 beta-lactamase is the polypeptide having the sequence shown in SEQ ID NO:1. This enzyme has been described in 2000 by Poirel et al. (Characterization of VIM-2, a carbapenemhydrolyzing metallo-beta-lactamase and its plasmid- and integron-borne gene from a *Pseudomonas aeruginosa* clinical isolate in France; Antimicrob. Agents Chemother. 2000; 44(4): 891-7) and further characterized by Docquier et al. in 2003 (On functional and structural heterogeneity of VIM-type metallo-beta-lactamases. J. Antimicrob. Chemother. 2003; 51:257-266).

The activity of the VIM-2 variant of the invention may be tested by a number of assays. For example, in vitro enzyme assays are implemented, in which the beta-lactam-hydrolyzing activity is determined spectrophotometrically in the presence of protein samples containing the wild-type VIM-2 or a VIM-2 variant. Specifically, the concentration of a beta-lactam compound and/or its hydrolysis product in solution (using a suitable buffer, such as 50 mM HEPES buffer, pH 7.5, supplemented with 50 µM $ZnSO_4$) could be followed in a UV-Visible spectrophotometer or microwell plate reader at a wavelength that corresponds to the maximum absorbance of the substrate and/or product. In the presence of a beta-lactamase, the time-dependent variation of the concentration of the beta-lactam substrate and/or product will thus correspond to the reaction rate. If the initial rate of hydrolysis is measured ($[S]_t \approx [S]_0$), this reaction rate (expressed in µM/min or µM/s) is directly proportional to the enzyme concentration in the assayed sample. Furthermore, the variation of the initial rate upon initial substrate concentration is characterized by the Henri-Michaelis-Menten equation and allows to compute the kinetic parameters ($k_{cat}$ and $K_M$) of the enzyme for the hydrolysis of specific beta-lactam compounds. Thus, the measure of the initial rates of hydrolysis, as determined in such enzyme assays, allows to characterize the properties of samples containing VIM-2 variants, such as its preferential activity towards a specific substrate or its relative abundance in the sample.

In a particular embodiment, the polypeptide of the present invention may be isolated. In the context of the present invention, the term "isolated" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE. In particular, it is preferred that the polypeptides are in "essentially pure form", i.e., that the polypeptide preparation is essentially free of other biochemical components such as lipids, nucleic acids, polysaccharides and polypeptides that may be present in unpurified extracts containing the polypeptide of interest. This can be accomplished, for example, by preparing the polypeptide by means of well-known recombinant methods and by classical purification methods.

The relatedness between two amino acid sequences is described by the parameter "identity". For purposes of the present invention, the alignment of two amino acid sequences is determined by using the Needle program from the EMBOSS package (http://emboss.org) version 2.8.0. The Needle program implements the global alignment algorithm described in Needleman and Wunsch, 1970, J. Mol. Biol. 48: 443-453. The substitution matrix used is BLOSUM62, gap opening penalty is 10, and gap extension penalty is 0.5.

The degree of identity between an amino acid sequence of the present invention and the amino acid sequence referred to in the claims (SEQ ID NO:1) is calculated as the number of exact matches in an alignment of the two sequences, divided by the length of the "invention sequence" or the length of SEQ ID NO:1, whichever is the shortest. The result is expressed in percent identity.

An exact match occurs when the "invention sequence" and SEQ ID NO:1 have identical amino acid residues in the same positions of the alignment. The length of a sequence is the number of amino acid residues in the sequence (e.g., the length of amino acids 1-240 of SEQ ID NO:1 is 240).

In particular embodiments of the present invention, the degree of identity of those particular polypeptides to SEQ ID NO:1 is at least 70%, 75%, 80%, 85%, 90%, 91%, 92%, 93%, 94%, 95%, 96%, 97%, 98% or at least 99%. In still further embodiments, their degree of identity to SEQ ID NO:1 is of at least 88.7%, 89.1%, 89.5%, 89.8%, 90.2%, 90.6%, 91%, 91.4%, 91.7%, 92.1%, 92.5%, 92.9%, 93.2%, 93.6%, 94%, 94.4%, 94.7%, 95.1%, 95.5%, 95.9%, 96.2%, 96.6%, 97%, 97.4%, 97.7%, 98.1%, 98.5%, 98.9%, 99.2% or at least 99.6%.

Of course, the VIM-2 variant of the present invention may further comprise a number of modifications relative to SEQ ID NO:1 in positions different from those specifically identified above. Further modifications may include amino acid substitutions, deletions or insertions, as well as combinations of any number of such modifications. In a particular embodiment, the VIM-2 variant of the present invention includes amino acid deletions in its N-terminal or further amino acid deletions in its C-terminal end, relative to SEQ ID NO:1, in addition to those specifically identified above. In an illustrative, non-limiting, embodiment, the polypeptide of the invention may be deleted of further 1, 2, 3, or 4 C-terminal amino acids in addition to those specifically mentioned as truncated above. In another illustrative, non-limiting embodiment, the polypeptide of the invention may be deleted of one or more than one (such as 1, 2, 3, 4, 5, 6 or 7 amino acids located at the amino-terminal end of the protein, as compared to SEQ ID NO:1, i.e. as compared to a sequence of wild-type VIM-2 that has undergone N-terminal signal peptide cleavage (i.e. the sequence of wild-type VIM-2 without its signal peptide). In a specific variant of this embodiment, the polypeptide that is deleted (or, otherwise stated, that has a truncation) of one or more than one amino acids located at the amino-terminal end as compared to SEQ ID NO:1 may further comprise an insertion or extension as is defined below, such as a tag or a signal peptide.

In the context of the present invention, the term "insertion" is intended to also cover N- and/or C-terminal extensions. In a particular embodiment, N-terminal extensions may include the addition of a signal peptide to the polypeptide of the invention. This may include the natural signal peptide of wild-type VIM-2 having the amino acid sequence MFKLLSKLLVYLTASIMAIASPLAFS (SEQ ID NO:2) or a modified signal peptide having either of substitutions L9S, L9F, L9W, V10I, L12C, A14V, I16T, M17L, I19M, I19T, F25C when compared to that of wild-type VIM-2, or any combination of the above mentioned substitutions, or any other appropriate signal peptide, or both.

Representative N-terminal or C-terminal extensions may include the addition of non-naturally occurring amino acid (s), such as "tag" peptides encoded by a DNA fragment cloned in fusion with the wild-type VIM-2 or any variant thereof, which allows facilitating the identification and/or purification of the polypeptide of the invention. Such appropriate tags may include histidine tags (6×His) or glutathione-S-transferase or maltose-binding protein, for example, as is well known in the art.

A polypeptide according to the invention may present a specific activity for a given beta-lactam antibiotic improved as compared to the specific activity exhibited by wild-type VIM-2 of SEQ ID NO:1 for the same antibiotic. In a particular embodiment, the specific activity, expressed in nmoles of substrate hydrolyzed per unit of time and per mg of a protein sample containing the polypeptide of the present invention is at least 105%, relative to the specific activity of the wild-type VIM-2 of SEQ ID NO:1 determined using the same procedure exposed in the example section. In a further embodiment, the relative specific activity of the polypeptide of the present invention is at least 110, 115, 120, 125, 130, 135, 140, 145, 150, 160, 170, 180, 190, 200, 220, 240, 260, 280, 300, 350, 400, 500, 600, 700, 800 or even at least 1600%, still relative to the specific activity of wild-type VIM-2 of SEQ ID NO:1.

In a further particular embodiment, the polypeptide of the invention comprises, or consists of, the amino acid sequence of any one of SEQ ID NO: 3 to 6, or a fragment thereof having beta-lactamase activity (such as a fragment lacking 1, 2, 3 or 4 or more than 4 C-terminal amino acids as compared to the polypeptide of any one of SEQ ID NO:3 to 6) (being understood that the polypeptide comprising SEQ ID NO:3 to 6 is not the wild-type VIM-2 sequence). In a variant of this embodiment, the polypeptide without a signal peptide may comprise a further amino acid substitution. In another variant of this embodiment, the polypeptide further comprises a signal peptide (such as the signal peptide shown in SEQ ID NO:2 or any variant thereof as defined above) at its N-terminal end.

| SEQ ID | sequence description |
|---|---|
| SEQ ID NO: 1 | Wild-type VIM-2 enzyme |
| SEQ ID NO: 2 | Signal peptide |
| SEQ ID NO: 3 | C-terminal truncation from position 236 |
| SEQ ID NO: 4 | C-terminal truncation from position 236 + Q34R substitution |
| SEQ ID NO: 5 | C-terminal truncation from position 236 (starting with a V as the most N-terminal amino acid) |
| SEQ ID NO: 6 | C-terminal truncation from position 236 + Q34R substitution (starting with a V as the most N-terminal amino acid) |

The present invention also relates to a nucleic acid molecule comprising a nucleic acid sequence which encodes a VIM-2 polypeptide variant of the invention.

The term "isolated nucleic acid sequence" refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose gel electrophoresis or any other appropriate method. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The nucleic acid sequences of the invention can be prepared by introducing at least one mutation into a template sequence encoding wild-type VIM-2 of SEQ ID NO:1 or a subsequence thereof, wherein the mutant nucleic acid sequence encodes a variant VIM-2 polypeptide. The introduction of a mutation into the nucleic acid sequence to exchange one nucleotide for another nucleotide may be accomplished by any of the methods known in the art, e.g., by site-directed mutagenesis, by random mutagenesis, or by doped, spiked, or localized random mutagenesis.

Random mutagenesis is suitably performed either as localized or region-specific random mutagenesis in at least three parts of the gene translating to the amino acid sequence shown in question, or within the whole gene. When the mutagenesis is performed by the use of an oligonucleotide, the oligonucleotide may be doped or spiked with the three non-parent nucleotides during the synthesis of the oligonucleotide at the positions which are to be changed. The doping or spiking may be performed so that codons for unwanted amino acids are avoided. The doped or spiked oligonucleotide can be incorporated into the DNA encoding the polypeptide by any technique, using, e.g., PCR, LCR or any DNA polymerase and ligase, or other DNA processing/modifying enzyme, such as a topoisomerase, as deemed appropriate.

Preferably, the doping is carried out using "constant random doping", in which the percentage of wild-type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints.

The random mutagenesis may be advantageously localized to a part of the parent VIM-2 sequence in question. This may, e.g., be advantageous when certain regions of the enzyme have been identified to be of particular importance for a given property of the enzyme.

Alternative methods for providing variants of the invention include gene shuffling e.g., as described in WO 95/22625 or in WO 96/00343, and the consensus derivation process as described in EP 897985.

The invention further relates to a nucleic acid construct comprising a nucleic acid sequence of the present invention operably linked to one or more control sequences which direct the expression of the coding sequence in a suitable prokaryotic or eukaryotic host cell under conditions compatible with the control sequences. Expression will be understood to include any step involved in the production of the polypeptide including, but not limited to, transcription, post-transcriptional modification, translation, post-translational modification, and secretion.

The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention. In a particular embodiment, the nucleic acid construct or expression cassette is comprised within a plasmid (such as an expression plasmid).

The term "control sequences" is defined herein to include all components which are necessary or advantageous for the expression of a polynucleotide encoding a polypeptide of the present invention. Each control sequence may be native or foreign to the nucleotide sequence encoding the polypeptide. Such control sequences include, but are not limited to, a leader, an operator, propeptide sequence, promoter, transcription initiation sequence, translation initiation sequence, signal peptide sequence, translation termination sequence, polyadenylation sequence and transcription terminator. At a minimum, the control sequences include a promoter, and transcriptional stop signal, and translational initiation and stop signals. The control sequences may be provided with linkers for the purpose of introducing specific restriction sites facilitating ligation of the control sequences with the coding region of the nucleotide sequence encoding a polypeptide.

The term "operably linked" denotes herein a configuration in which a control sequence is placed at an appropriate position relative to the coding sequence of the polynucleotide sequence such that the control sequence directs the expression of the coding sequence of a polypeptide.

When used herein the term "coding sequence" (CDS) means a nucleotide sequence, which directly specifies the amino acid sequence of its protein product. The boundaries of the coding sequence are generally determined by an open reading frame, which usually begins with the ATG start codon or alternative start codons such as GTG and TTG, and usually terminates with a stop codon such as TAA, TGA or TAG. The coding sequence may consist in a DNA, cDNA, or recombinant nucleotide sequence; it may be natural, semisynthetic or synthetic; it may also contain unnatural or modified nucleotides.

The term "expression" includes any step involved in the production of the polypeptide including, but not limited to, transcription, post-transcriptional modification, translation, post-translational modification, and secretion.

The term "expression vector" is defined herein as a linear or circular DNA molecule that comprises a polynucleotide encoding a polypeptide of the invention, which is operably linked to additional nucleotides that provide for its expression.

A nucleic acid sequence encoding a polypeptide of the invention can be expressed using an expression vector which typically includes control sequences encoding a promoter, operator, ribosome binding site, translation initiation signal, and, optionally, a repressor gene or various activator genes.

The recombinant expression vector carrying the DNA sequence encoding a polypeptide according to the invention may be any vector which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated. It may also remain in the cell as an autonomously replicating extra-chromosomal DNA molecule, such as a plasmid.

The invention further relates to a host cell comprising the nucleic acid sequence or the nucleic acid construct of the invention. A "host cell", as used herein, includes any cell type, prokaryotic or eukaryotic, which is susceptible to transformation, transfection, transduction, infection and the like with a nucleic acid construct comprising a polynucleotide of the present invention.

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector. The term "host cell" encompasses any progeny of a parent cell that is not identical to the parent cell due to mutations that occur during replication. The choice of a host cell will to a large extent depend upon the gene encoding the polypeptide and its source. The host cell may consist in or originate from a unicellular or polycellular organism, and may be prokaryotic or eukaryotic.

Among useful unicellular microorganisms are bacterial cells such as Gram-positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* and *Streptomyces murinus*, or Gram-negative bacteria such as *E. coli* and *Pseudomonas* sp.

The introduction of a vector into a bacterial host cell may, for instance, be effected by protoplast transformation (see, e.g., Chang and Cohen, 1979, Molecular General Genetics 168: 111-115), by DNA transformation using competent cells (see, e.g., Young and Spizizin, 1961, Journal of Bacteriology 81: 823-829, or Dubnau and Davidoff-Abelson, 1971, Journal of Molecular Biology 56: 209-221) using any method of transformation including but not limited to chemical transformation or electroporation (see, e.g., Shigekawa and Dower, 1988, Biotechniques 6: 742-751), or conjugation (see, e.g., Koehler and Thorne, 1987, Journal of Bacteriology 169: 5771-5278).

The host cell may also be from a eukaryote, such as an animal, and in particular mammalian, an insect, a plant, or cell-lines derived thereof, or a unicellular eukaryote or fungal cell. The recombinant protein may also be produced in a multicellular organism, such as an animal, in particular a mammal, or a plant.

In a particular embodiment, the host cell may be a fungal cell. In a particular embodiment, the fungal host cell is *Saccharomyces cerevisiae* or *Pichia pastoris*. In a particular embodiment, the host cell is a cell line originating from Chinese Hamster Ovary cells.

Fungal cells may be transformed by a process involving protoplast formation, transformation of the protoplasts, and regeneration of the cell wall in a manner known per se. Yeast may be transformed using the procedures described by Becker and Guarente, In Abelson, J. N. and Simon, M. I., editors, Guide to Yeast Genetics and Molecular Biology, Methods in Enzymology 194: 182-187, Academic Press, Inc., New York; Ito et al., 1983, Journal of Bacteriology 153: 163; and Hinnen et al., 1978, Proceedings of the National Academy of Sciences USA 75: 1920. Fungal cells may also be transformed by electroporation, or any other suitable method for introducing DNA molecules into a cell.

The present invention also relates to methods for producing a polypeptide of the present invention comprising (a) cultivating a host cell under conditions conducive for production of the polypeptide; and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermenters performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). In some cases, the conditions for growth of the host cells, and production of the polypeptide are distinct; in a first phase the host cells are allowed to multiply under appropriate conditions, and in a second phase conditions may be changed to allow optimal production of the polypeptide. If the polypeptide is secreted into the nutrient medium, the polypeptide can be recovered directly from the medium. If the polypeptide is not secreted, it can be recovered from cell lysates.

The resulting polypeptide may be recovered using methods known in the art. For example, the polypeptide may be recovered from the nutrient medium by conventional procedures including, but not limited to, centrifugation, filtration, extraction, adsorption, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing, preparative gel electrophoresis), differential solubility (e.g., ammonium sulfate precipitation), extraction (see, e.g., Protein Purification, J.-C. Janson and Lars Ryden, editors, VCH Publishers, New York, 1989), or a combination thereof.

The present invention further relates to a composition comprising a polypeptide of the present invention. Appropriate compositions include a polypeptide as defined above, in combination with an acceptable carrier. The compositions may be prepared according to methods well known in the art, and be in the form of liquid or dry compositions. The composition may further include components which stabilize the polypeptide according to the invention such as glycerol.

In a particular embodiment, the composition is a pharmaceutical composition comprising a pharmaceutically acceptable carrier. The composition may be in the form of a composition which is orally administrable and is able to release the polypeptide in a desired part of the gastrointestinal tract of a subject in need thereof. Preferably, the desired part is the stomach, duodenum, jejunum, ileum, caecum or colon. In a preferred embodiment, the desired part of the intestine is the jejunum, the ileum, the caecum or the colon, more preferably the ileum, the caecum or the colon. In the latter case, the composition may include one or more gastro resistant compounds which protect the polypeptide of the invention from gastric juice. Such compositions may include the drug delivery systems described in WO93/13795, WO2004/016248 or US20050249716, among others.

The present invention further relates to a host cell or organism as described above, producing the polypeptide of the present invention, that can be introduced into the desired part of the intestine and is able to release said polypeptide into the desired part of the intestine of a subject in need thereof. In a preferred embodiment, the desired part of the intestine is the ileum, caecum or colon, more preferably the caecum or colon. Therefore, the present invention also relates to a host cell or organism as defined above, for use in a method of therapy as disclosed herein, wherein said host cell is administered to a subject in need thereof.

As mentioned above, the VIM-2 polypeptide variant of the present invention is useful in a number of therapeutic and non-therapeutic uses.

The present invention discloses methods of therapy implementing the polypeptide of the invention, wherein said polypeptide or a composition or a kit-of-parts containing the same in combination with an antibiotic, or a host cell or organism expressing said polypeptide is used in a method for inactivating a beta-lactam compound such as a beta-lactam antibiotic in a subject in need thereof. The method is implemented to treat or prevent the adverse effects of antibiotics such as intestinal dysbiosis, the selection of resistant bacteria, disruption of normal digestive processes, colonization by opportunistic intestinal pathogens such as *Clostridium difficile*, antibiotic-associated diarrhea or other diseases related to the intestinal dysbiosis.

The invention also relates to the use of the polypeptide, the composition, the host cell or organism, or the kit-of-parts of the invention, in a method for the treatment of a bacterial infection which is caused by bacteria which are susceptible to a beta-lactam antibiotic. More particularly, the bacterial infection is treated by using a combination of the polypeptide of the invention and a beta-lactam antibiotic which is sensitive to said polypeptide, thereby having the infection treated thanks to the beta-lactam antibiotic whereas any unwanted residual antibiotic is eliminated thanks to the polypeptide of the invention. In this particular embodiment, the polypeptide is preferably formulated in a composition that is able to release the polypeptide in a desired part of the intestine of a subject in need of such bacterial infection treatment, wherein the desired part of the intestine is preferably the jejunum, the ileum, the caecum or the colon, most preferably the ileum, the caecum or the colon. The polypeptide may also be released in the desired part of the intestine by a host cell or organism producing said polypeptide, wherein the desired part of the intestine is the ileum, caecum or colon, preferably the caecum or colon. In a particular aspect, the polypeptide, the composition, the host cell or organism, or the kit-of-parts of the invention is used for the treatment of a bacterial infection in a subject that may be an animal, a mammal or a human being whereby an antibiotic sensitive to said polypeptide is administered to the subject before, after or concomitantly with the administration of said polypeptide or composition thereof.

Other uses of the polypeptide of the invention include non-therapeutic uses such as the use of the polypeptide for the remediation of antibiotic in the environment or an environmental setting. Such uses and methods may be found described for example in WO 2012/007536 describing the use of laccases, cellulases and lipases for the remediation of antibiotics in the environment, and are herein applied mutatis mutandis for the elimination of beta-lactam antibiotics from the environment using the polypeptide of the invention.

LEGEND OF THE FIGURES

FIG. 1 is a graph representing the specific activity of wild-type VIM-2, VIM-2 DCT236 and VIM-2$_{[Q34R]}$ DCT236 variants after 0, 30, 60, 90, 120 and 240 minutes in piglets ileal medium.

EXAMPLES

Example 1: Determination of the Positions of Interest in the Sequence of VIM-2 Enzyme In order to identify amino acid positions relevant for either the enzyme activity, its substrate profile, its stability or its level of production in the host cell, random mutagenesis was used to create a library of bla$_{VIM-2}$ genes carrying up to 12 mutations. To this end, bla$_{VIM-2}$ mutants were introduced using an error-prone polymerase chain reaction, in the presence of nucleotide analogues. The bla$_{VIM-2}$-derived nucleotide sequences were then cloned in a suitable *Escherichia coli* plasmid vector and the properties of the enzyme carrying various substitutions (thus a laboratory variants deriving from the introduction of mutations in the bla$_{VIM-2}$ nucleotide sequence) were analyzed using the evaluation of the beta-lactam susceptibility profiles of the strains producing the variants, the determination of the specific-hydrolyzing activity for the degradation of various beta-lactams and the stability of the variant enzyme.

From the experiments described above performed on wild-type VIM-2, the following positions were discovered as positions of interest in the VIM-2 sequence wherein the positions correspond to the positions of the beta-lactamase represented in SEQ ID NO:1: positions 34 and 236.

Example 2: Production and Purification of One VIM-2 Variant at One Position

The VIM-2 variant was produced in *Escherichia coli* using either a P$_{lac}$-promoter-based system (using pLB-II high copy number plasmid, as described in Borgianni et al., *Antimicrob. Agents Chemother.*; 2010; 54:3197-3204) or a T7 promoter-based expression system (using the pET-9a expression plasmid). Briefly, the mutant bla$_{VIM-2}$ gene was cloned in the plasmid vector pLB-II or pET-9a using the NdeI and BamHI restriction sites, and the resulting plasmid introduced in *E. coli* DH5α or BL21(DE3) cells by electroporation. The resulting host cell was grown in either Luria-Bertani medium or the rich auto-inducing cell culture medium ZYP-5052 (Studier, F. W. 2005. Protein production by auto-induction in high density shaking cultures. Protein Expr. Purif 41:207-234) for 24 h, and the culture supernatant clarified by centrifugation. The resulting sample was then concentrated by ultrafiltration and loaded on an anion exchange chromatography column. Proteins were eluted using a linear NaCl gradient and the active fractions pooled and concentrated. The protein sample was then loaded on a gel filtration column and the proteins eluted with 50 mM HEPES (pH 7.5) supplemented with 50 µM ZnSO$_4$. The purified protein was then concentrated to 1-2 mg/ml and stored at −20° C.

All the mutants characterized in the following examples have been produced with a similar method. In particular, this production protocol was successfully used to produce the following variant VIM-2 enzymes: VIM-2 DCT236 (with a C-terminal deletion from position 236, i.e. the variant does not comprise amino acid 236-240 of wild-type VIM-2 of SEQ ID NO:1), VIM-2$_{[Q34R]}$, VIM-2$_{[Q34R]}$ DCT236.

Example 3: Determination of the Increased Resistance to Protease for Variants of VIM-2 Enzyme To measure the sensitivity of purified enzyme preparations (e. g. VIM-2, VIM-2 DCT236 and variants thereof, prepared as described in Example 2) to proteolytic degradation by commercially-available purified proteases, the enzyme (final concentration, 50 µg/mL) was incubated, at 35° C., for up to 150 min in a buffer (50 mM HEPES, 50 µM ZnSO4, pH 7.5) containing up to 2.5 mg/mL of trypsin (from bovine pancreas, Type III, Sigma-Aldrich Cat. No. T-8253).

The residual activity of the resulting sample was determined by means of a spectrophotometric assay, in which the hydrolysis rate of a 150 µM imipenem solution (in 50 mM HEPES, 50 µM ZnSO4, pH 7.5) was measured and compared to that of the sample at the beginning of the incubation (time, 0 min) or in the absence of protease.

In these conditions and in the absence of trypsin in the buffer, both tested enzymes (VIM-2 and VIM-2 DCT236) incubated for up to 150 min show a residual activity of 100±15%, indicated a good intrinsic stability of the enzymes in the buffer system used in these experiments. In the presence of 2.5 mg/mL trypsin, the VIM-2 only retains 70 and 66±10% of its initial activity after 30 or 90 min of incubation, respectively. By contrast, the VIM-2 DCT236 shows a residual activity of 98±10% in the presence of 2.5 mg/mL trypsin, even after 150 min of incubation. These data show that the VIM-2 DCT236 enzyme is less susceptible to trypsin-mediated proteolytic degradation than the VIM-2 enzyme.

Example 4: Determination of Increased Stability of Several Variants of VIM-2

To measure the stability of VIM-2 variants in intestinal samples (i. e. where the enzyme is for example intended to exert its hydrolytic activity), the following procedure is applied: the imipenem-hydrolyzing activity of purified enzymes was determined after incubation within ileal medium collected from piglets. The specific activity (Sp. Act.) for the variants was measured at different time points (0, 30, 60, 90, 120 and 240 min) during the incubation. The specific activity at time t was compared with the specific activity at time t=0 to assess the loss of activity of the variant in the intestinal medium. The residual activity at different time points could be compared to evaluate the greater stability in intestinal medium of some variants compared to the wild-type enzyme.

The specific activity of wild-type VIM-2 enzyme and VIM-2 variants VIM-2 DCT236 and $VIM-2_{[Q34R]}$ DCT236 over time when incubated in ileal medium are presented in FIG. 1.

As shown in FIG. 1, the wild-type enzyme lost 88% of its activity after 240 minutes incubation in ileal medium. The $VIM-2_{[Q34R]}$ DCT236 variant lost only 45% of its activity in the same conditions. The VIM-2 DCT236 variant lost only 80% of its activity in the same conditions.

Example 5: Determination of the Specific Activity of Given VIM-2 Variants Against Beta-Lactams For the mutant enzymes produced as mentioned in example 3, it is possible to measure the specific activity against specific beta-lactam compounds such as specific beta-lactam antibiotics. The specific activity assessment is performed as described hereafter: the hydrolysis of beta-lactams in the presence of crude extracts, prepared from bacterial cultures in the log or stationary growth phase as previously described (Docquier J.-D. et al., *J. Antimicrob. Chemother;* 2003; 51:257-266), containing a VIM-2 variant and/or purified VIM-2 variants was monitored spectrophotometrically at a suitable wavelength. The specific activity may be expressed in nmol of beta-lactam substrate hydrolyzed by min and per mg of total protein in the sample.

In the following, all the specific activities will be expressed relatively to the specific activity of the wild-type enzyme measured in the same conditions.

For VIM-2 variants, the measured specific activities are:

| Enzyme | (Specific activity of the enzyme/ Specific activity of the wild-type enzyme) for ampicillin |
|---|---|
| VIM-2$_{[WT]}$ | 1 |
| VIM-2$_{[Q34R]}$ | 10.06 |

| Enzyme | (Specific activity of the enzyme/ Specific activity of the wild-type enzyme) for piperacillin |
|---|---|
| VIM-2$_{[WT]}$ | 1 |
| VIM-2$_{[Q34R]}$ | 4.14 |

| Enzyme | (Specific activity of the enzyme/ Specific activity of the wild-type enzyme) for ceftazidime |
|---|---|
| VIM-2$_{[WT]}$ | 1 |
| VIM-2$_{[Q34R]}$ | 17 |

| Enzyme | (Specific activity of the enzyme/ Specific activity of the wild-type enzyme) for imipenem |
|---|---|
| VIM-2$_{[WT]}$ | 1 |
| VIM-2 DCT236 | 1.63 |
| VIM-2$_{[Q34R]}$ | 1.47 |

| Enzyme | (Specific activity of the enzyme/ Specific activity of the wild-type enzyme) for meropenem |
|---|---|
| VIM-2$_{[WT]}$ | 1 |
| VIM-2$_{[Q34R]}$ | 8.72 |

The invention claimed is:

1. An isolated polypeptide having beta-lactamase activity, which comprises an amino acid sequence having at least 90% sequence identity to SEQ ID NO:1, said amino acid sequence further comprising a substitution at a position corresponding to residue 34 in SEQ ID NO: 1 and a C-terminal truncation of residues 237-240 of SEQ ID NO:1.

2. The polypeptide according to claim 1, which comprises:
   a C-terminal truncation of residues 236-240 of SEQ ID NO:1, or
   a C-terminal truncation of residues 235-240 of SEQ ID NO:1.

3. The polypeptide according to claim 1, wherein said substitution is Q34R.

4. An isolated polypeptide having beta-lactamase activity, which comprises an amino acid sequence having at least 90% sequence identity to SEQ ID NO:1, and which comprises a C-terminal truncation of exactly five residues from position 236 to 240 of SEQ ID NO:1.

5. The polypeptide according to claim 1, wherein the first residue of SEQ ID NO:1 is replaced with a methionine residue.

6. The polypeptide according to claim 1, further comprising a signal peptide at its N-terminal end having the sequence of SEQ ID NO:2.

7. The polypeptide according to claim 1, comprising a truncation at its N-terminal end as compared to the sequence of SEQ ID NO:1.

8. The polypeptide according to claim 1, consisting of the amino acid sequence of any one of SEQ ID NO:3 to 6.

9. A composition comprising the polypeptide of claim 1.

10. The composition of claim 9, which is orally administrable and is able to release the polypeptide in the intestine.

11. A kit-of-parts comprising
   (a) the composition of claim 10; and
   (b) a beta-lactam antibiotic which is sensitive to said polypeptide contained in the composition of (a);
   for separate, sequential or simultaneous administration.

12. The composition of claim 9, which is orally administrable and is able to release the polypeptide in the jejunum, the ileum, the caecum or the colon.

13. The polypeptide according to claim 1, comprising the amino acid sequence of any one of SEQ ID NO:3 to 6.

14. A method of treatment comprising administering the polypeptide of claim 1 to a patient.

15. The method of claim 14, wherein the patient has a bacterial infection which is caused by a bacteria which is susceptible to a beta-lactam antibiotic.

16. The method of claim 14, comprising administering the polypeptide in combination with a beta-lactam antibiotic which is sensitive to said polypeptide.

* * * * *

SEQUENCE LISTING

```
<160> NUMBER OF SEQ ID NOS: 6

<210> SEQ ID NO 1
<211> LENGTH: 240
<212> TYPE: PRT
<213> ORGANISM: artificial
<220> FEATURE:
<223> OTHER INFORMATION: wild-type VIM-2

<400> SEQUENCE: 1

Val Asp Ser Ser Gly Glu Tyr Pro Thr Val Ser Glu Ile Pro Val Gly
1               5                   10                  15

Glu Val Arg Leu Tyr Gln Ile Ala Asp Gly Val Trp Ser His Ile Ala
                20                  25                  30

Thr Gln Ser Phe Asp Gly Ala Val Tyr Pro Ser Asn Gly Leu Ile Val
            35                  40                  45

Arg Asp Gly Asp Glu Leu Leu Leu Ile Asp Thr Ala Trp Gly Ala Lys
50                  55                  60

Asn Thr Ala Ala Leu Leu Ala Glu Ile Glu Lys Gln Ile Gly Leu Pro
65                  70                  75                  80

Val Thr Arg Ala Val Ser Thr His Phe His Asp Asp Arg Val Gly Gly
                85                  90                  95

Val Asp Val Leu Arg Ala Ala Gly Val Ala Thr Tyr Ala Ser Pro Ser
            100                 105                 110

Thr Arg Arg Leu Ala Glu Val Glu Gly Asn Glu Ile Pro Thr His Ser
        115                 120                 125

Leu Glu Gly Leu Ser Ser Ser Gly Asp Ala Val Arg Phe Gly Pro Val
130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
                165                 170                 175

Leu Ser Arg Thr Ser Ala Gly Asn Val Ala Asp Ala Asp Leu Ala Glu
            180                 185                 190
```

```
Trp Pro Thr Ser Ile Glu Arg Ile Gln Gln His Tyr Pro Glu Ala Gln
        195                 200                 205

Phe Val Ile Pro Gly His Gly Leu Pro Gly Gly Leu Asp Leu Leu Lys
210                 215                 220

His Thr Thr Asn Val Val Lys Ala His Thr Asn Arg Ser Val Val Glu
225                 230                 235                 240

<210> SEQ ID NO 2
<211> LENGTH: 26
<212> TYPE: PRT
<213> ORGANISM: artificial
<220> FEATURE:
<223> OTHER INFORMATION: VIM-2 signal peptide

<400> SEQUENCE: 2

Met Phe Lys Leu Leu Ser Lys Leu Leu Val Tyr Leu Thr Ala Ser Ile
1               5                   10                  15

Met Ala Ile Ala Ser Pro Leu Ala Phe Ser
            20                  25

<210> SEQ ID NO 3
<211> LENGTH: 235
<212> TYPE: PRT
<213> ORGANISM: artificial
<220> FEATURE:
<223> OTHER INFORMATION: VIM-2 variant

<400> SEQUENCE: 3

Met Asp Ser Ser Gly Glu Tyr Pro Thr Val Ser Glu Ile Pro Val Gly
1               5                   10                  15

Glu Val Arg Leu Tyr Gln Ile Ala Asp Gly Val Trp Ser His Ile Ala
                20                  25                  30

Thr Gln Ser Phe Asp Gly Ala Val Tyr Pro Ser Asn Gly Leu Ile Val
            35                  40                  45

Arg Asp Gly Asp Glu Leu Leu Leu Ile Asp Thr Ala Trp Gly Ala Lys
    50                  55                  60

Asn Thr Ala Ala Leu Leu Ala Glu Ile Glu Lys Gln Ile Gly Leu Pro
65                  70                  75                  80

Val Thr Arg Ala Val Ser Thr His Phe His Asp Asp Arg Val Gly Gly
                85                  90                  95

Val Asp Val Leu Arg Ala Ala Gly Val Ala Thr Tyr Ala Ser Pro Ser
            100                 105                 110

Thr Arg Arg Leu Ala Glu Val Glu Gly Asn Glu Ile Pro Thr His Ser
        115                 120                 125

Leu Glu Gly Leu Ser Ser Ser Gly Asp Ala Val Arg Phe Gly Pro Val
    130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
                165                 170                 175

Leu Ser Arg Thr Ser Ala Gly Asn Val Ala Asp Ala Asp Leu Ala Glu
            180                 185                 190

Trp Pro Thr Ser Ile Glu Arg Ile Gln Gln His Tyr Pro Glu Ala Gln
        195                 200                 205

Phe Val Ile Pro Gly His Gly Leu Pro Gly Gly Leu Asp Leu Leu Lys
    210                 215                 220

His Thr Thr Asn Val Val Lys Ala His Thr Asn
225                 230                 235
```

225           230           235

<210> SEQ ID NO 4
<211> LENGTH: 235
<212> TYPE: PRT
<213> ORGANISM: artificial
<220> FEATURE:
<223> OTHER INFORMATION: VIM-2 variant

<400> SEQUENCE: 4

Met Asp Ser Ser Gly Glu Tyr Pro Thr Val Ser Glu Ile Pro Val Gly
1               5                   10                  15

Glu Val Arg Leu Tyr Gln Ile Ala Asp Gly Val Trp Ser His Ile Ala
            20                  25                  30

Thr Arg Ser Phe Asp Gly Ala Val Tyr Pro Ser Asn Gly Leu Ile Val
        35                  40                  45

Arg Asp Gly Asp Glu Leu Leu Leu Ile Asp Thr Ala Trp Gly Ala Lys
    50                  55                  60

Asn Thr Ala Ala Leu Leu Ala Glu Ile Glu Lys Gln Ile Gly Leu Pro
65                  70                  75                  80

Val Thr Arg Ala Val Ser Thr His Phe His Asp Asp Arg Val Gly Gly
                85                  90                  95

Val Asp Val Leu Arg Ala Ala Gly Val Ala Thr Tyr Ala Ser Pro Ser
            100                 105                 110

Thr Arg Arg Leu Ala Glu Val Glu Gly Asn Glu Ile Pro Thr His Ser
        115                 120                 125

Leu Glu Gly Leu Ser Ser Gly Asp Ala Val Arg Phe Gly Pro Val
    130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
                165                 170                 175

Leu Ser Arg Thr Ser Ala Gly Asn Val Ala Asp Ala Asp Leu Ala Glu
            180                 185                 190

Trp Pro Thr Ser Ile Glu Arg Ile Gln Gln His Tyr Pro Glu Ala Gln
        195                 200                 205

Phe Val Ile Pro Gly His Gly Leu Pro Gly Gly Leu Asp Leu Leu Lys
    210                 215                 220

His Thr Thr Asn Val Val Lys Ala His Thr Asn
225                 230                 235

<210> SEQ ID NO 5
<211> LENGTH: 235
<212> TYPE: PRT
<213> ORGANISM: artificial
<220> FEATURE:
<223> OTHER INFORMATION: VIM-2 variant

<400> SEQUENCE: 5

Val Asp Ser Ser Gly Glu Tyr Pro Thr Val Ser Glu Ile Pro Val Gly
1               5                   10                  15

Glu Val Arg Leu Tyr Gln Ile Ala Asp Gly Val Trp Ser His Ile Ala
            20                  25                  30

Thr Gln Ser Phe Asp Gly Ala Val Tyr Pro Ser Asn Gly Leu Ile Val
        35                  40                  45

Arg Asp Gly Asp Glu Leu Leu Leu Ile Asp Thr Ala Trp Gly Ala Lys
    50                  55                  60

```
Asn Thr Ala Ala Leu Leu Ala Glu Ile Glu Lys Gln Ile Gly Leu Pro
 65                  70                  75                  80

Val Thr Arg Ala Val Ser Thr His Phe His Asp Asp Arg Val Gly Gly
                 85                  90                  95

Val Asp Val Leu Arg Ala Ala Gly Val Ala Thr Tyr Ala Ser Pro Ser
            100                 105                 110

Thr Arg Arg Leu Ala Glu Val Glu Gly Asn Glu Ile Pro Thr His Ser
        115                 120                 125

Leu Glu Gly Leu Ser Ser Gly Asp Ala Val Arg Phe Gly Pro Val
130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
                165                 170                 175

Leu Ser Arg Thr Ser Ala Gly Asn Val Ala Asp Ala Asp Leu Ala Glu
            180                 185                 190

Trp Pro Thr Ser Ile Glu Arg Ile Gln Gln His Tyr Pro Glu Ala Gln
        195                 200                 205

Phe Val Ile Pro Gly His Gly Leu Pro Gly Gly Leu Asp Leu Leu Lys
210                 215                 220

His Thr Thr Asn Val Val Lys Ala His Thr Asn
225                 230                 235

<210> SEQ ID NO 6
<211> LENGTH: 235
<212> TYPE: PRT
<213> ORGANISM: artificial
<220> FEATURE:
<223> OTHER INFORMATION: VIM-2 variant

<400> SEQUENCE: 6

Val Asp Ser Ser Gly Glu Tyr Pro Thr Val Ser Glu Ile Pro Val Gly
 1               5                  10                  15

Glu Val Arg Leu Tyr Gln Ile Ala Asp Gly Val Trp Ser His Ile Ala
                20                  25                  30

Thr Arg Ser Phe Asp Gly Ala Val Tyr Pro Ser Asn Gly Leu Ile Val
            35                  40                  45

Arg Asp Gly Asp Glu Leu Leu Leu Ile Asp Thr Ala Trp Gly Ala Lys
 50                  55                  60

Asn Thr Ala Ala Leu Leu Ala Glu Ile Glu Lys Gln Ile Gly Leu Pro
 65                  70                  75                  80

Val Thr Arg Ala Val Ser Thr His Phe His Asp Asp Arg Val Gly Gly
                 85                  90                  95

Val Asp Val Leu Arg Ala Ala Gly Val Ala Thr Tyr Ala Ser Pro Ser
            100                 105                 110

Thr Arg Arg Leu Ala Glu Val Glu Gly Asn Glu Ile Pro Thr His Ser
        115                 120                 125

Leu Glu Gly Leu Ser Ser Gly Asp Ala Val Arg Phe Gly Pro Val
130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
                165                 170                 175

Leu Ser Arg Thr Ser Ala Gly Asn Val Ala Asp Ala Asp Leu Ala Glu
            180                 185                 190
```

```
Trp Pro Thr Ser Ile Glu Arg Ile Gln Gln His Tyr Pro Glu Ala Gln
        195                 200                 205

Phe Val Ile Pro Gly His Gly Leu Pro Gly Gly Leu Asp Leu Leu Lys
    210                 215                 220

His Thr Thr Asn Val Val Lys Ala His Thr Asn
225                 230                 235
```